United States Patent
Suyama et al.

(10) Patent No.: US 8,964,939 B2
(45) Date of Patent: *Feb. 24, 2015

(54) RADIATION DETECTION DEVICE, RADIATION IMAGE ACQUIRING SYSTEM, RADIATION INSPECTION SYSTEM, AND RADIATION DETECTION METHOD

(75) Inventors: Toshiyasu Suyama, Hamamatsu (JP); Tadashi Maruno, Hamamatsu (JP); Toshihide Sasaki, Hamamatsu (JP); Junichi Sonoda, Hamamatsu (JP); Shinji Takihi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 322 days.

This patent is subject to a terminal disclaimer.

(21) Appl. No.: 13/534,426

(22) Filed: Jun. 27, 2012

(65) Prior Publication Data

US 2013/0016809 A1    Jan. 17, 2013

Related U.S. Application Data

(63) Continuation of application No. 12/615,305, filed on Nov. 10, 2009, now Pat. No. 8,223,922.

(30) Foreign Application Priority Data

Nov. 11, 2008  (JP) ................. P2008-288917

(51) Int. Cl.
*H05G 1/64* (2006.01)
*G01N 23/087* (2006.01)
(Continued)

(52) U.S. Cl.
CPC .............. *G01N 23/04* (2013.01); *G01V 5/0016* (2013.01); *G01V 5/0008* (2013.01); *G01N 2223/1016* (2013.01); *G01N 2223/306* (2013.01); *G01N 2223/3307* (2013.01)
USPC ............. 378/98.8; 378/53; 378/57; 378/98.9; 378/98.11; 378/98.12; 250/370.09

(58) Field of Classification Search
CPC .......... G01N 23/04; G01N 2223/1016; G01N 2223/3307; G01T 1/2018; G01T 1/24; G01T 1/2928; G01V 5/0041; G01V 5/0008; G01V 5/0016
USPC ............. 378/53, 57, 98.8, 98.9, 98.11, 98.12; 250/370.09

See application file for complete search history.

(56) References Cited

U.S. PATENT DOCUMENTS

| 4,445,226 A | 4/1984 | Brody |
|---|---|---|
| 5,481,584 A | 1/1996 | Tang et al. |

(Continued)

FOREIGN PATENT DOCUMENTS

| JP | 6-27249 | 2/1994 |
|---|---|---|
| JP | 7-306165 | 11/1995 |

(Continued)

OTHER PUBLICATIONS

Office Action dated Mar. 1, 2013 that issued in U.S. Appl. No. 13/600,516 including double patenting rejections at pp. 3-8.

(Continued)

*Primary Examiner* — Allen C. Ho
(74) *Attorney, Agent, or Firm* — Drinker Biddle & Reath LLP

(57) ABSTRACT

A radiation image acquiring system is provided. An X-ray image acquiring system irradiates X-rays to a subject from an X-ray source, and detects X-rays transmitted through the subject. The X-ray image acquiring system includes a first detector for detecting X-rays that are transmitted through the subject to generate first image data, a second detector arranged in parallel to the first detector with a dead zone region sandwiched therebetween, for detecting X-rays that are transmitted through the subject to generate second image data, and a timing control section for controlling detection timing of the second detector based on a dead zone width of the dead zone region so that first image data to be generated by the first detector and second image data to be generated by the second detector mutually correspond.

20 Claims, 12 Drawing Sheets

(51) Int. Cl.
*G01N 23/04* (2006.01)
*G01V 5/00* (2006.01)

(56) References Cited

U.S. PATENT DOCUMENTS

| | | | |
|---|---|---|---|
| 5,570,403 | A | 10/1996 | Yamazaki et al. |
| 5,841,832 | A | 11/1998 | Mazess et al. |
| 6,188,747 | B1 | 2/2001 | Geus et al. |
| 6,198,795 | B1 | 3/2001 | Naumann et al. |
| 6,370,223 | B1 | 4/2002 | Gleason et al. |
| 6,600,805 | B2 | 7/2003 | Hansen |
| 6,856,667 | B2 * | 2/2005 | Ellengogen ............ 378/57 |
| 7,724,869 | B2 | 5/2010 | Wang et al. |
| 8,223,922 | B2 | 7/2012 | Suyama et al. |
| 8,280,005 | B2 | 10/2012 | Suyama et al. |
| 8,600,005 | B2 * | 12/2013 | Suyama et al. ......... 378/98.8 |
| 2002/0168046 | A1 | 11/2002 | Hansen |
| 2010/0119040 | A1 | 5/2010 | Suyama et al. |

FOREIGN PATENT DOCUMENTS

| | | |
|---|---|---|
| JP | 8-68768 | 3/1996 |
| JP | 10-318943 | 12/1998 |
| JP | 11-316198 | 11/1999 |
| JP | 2001-99790 | 3/2001 |
| JP | 2001-99790 | 4/2001 |
| JP | 2002-168803 | 6/2002 |
| JP | 2003-279503 | 10/2003 |
| JP | 2006-126154 | 5/2006 |
| JP | 5559471 | 7/2014 |
| TW | 200841008 | 10/2008 |
| TW | 200842393 | 11/2008 |

OTHER PUBLICATIONS

U.S. Office Action dated Apr. 13, 2012, issued in U.S. Appl. No. 12/615,675 filed Nov. 10, 2009.

* cited by examiner

Fig.9
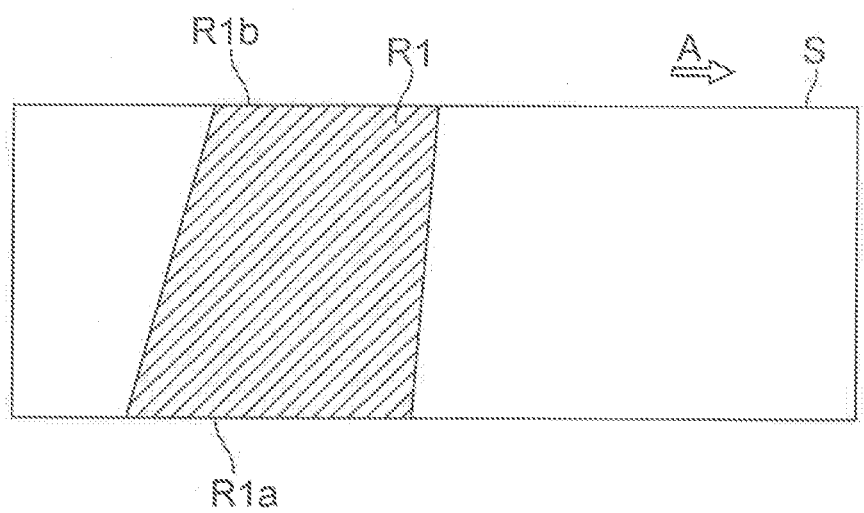
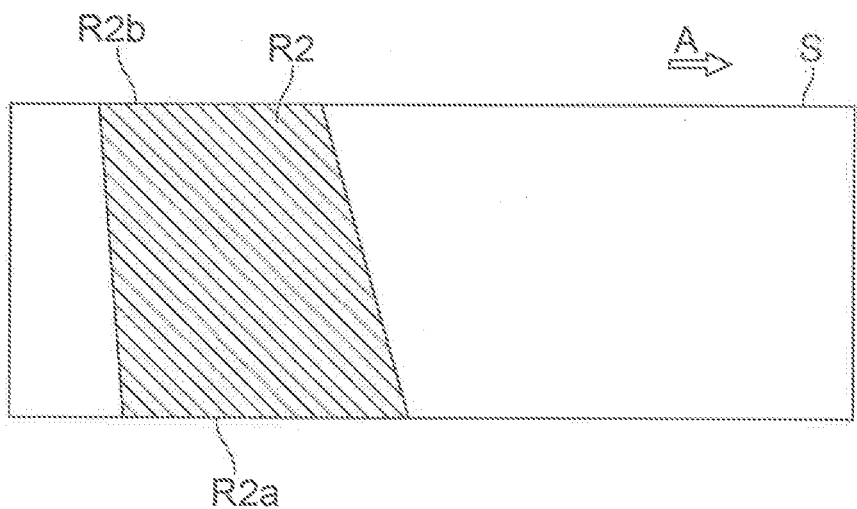

RADIATION DETECTION DEVICE, RADIATION IMAGE ACQUIRING SYSTEM, RADIATION INSPECTION SYSTEM, AND RADIATION DETECTION METHOD

This is a continuation application of prior application Ser. No. 12/615,305, filed on Nov. 10, 2009, which has been patented as U.S. Pat. No. 8,223,922 B2, issued on Jul. 17, 2012, which is incorporated by reference herein in its entirety.

BACKGROUND OF THE INVENTION

1. Field of the Invention

The present invention relates to a radiation detection device, a radiation image acquiring system, a radiation inspection system, and a radiation detection method.

2. Related Background Art

Conventionally, it has been common to allow X-rays to transmit through a subject being a specimen such as food or drugs and make an inspection based on a transmission X-ray image thereof to determine the existence of a foreign substance in a subject. For such an inspection, an X-ray image acquiring device including an X-ray source for irradiating X-rays to the subject and a linear line sensor for detecting a transmission image of X-rays irradiated to the subject from the X-ray source has been used.

However, in the case of detection of transmitted X-rays by a single line sensor with no energy discrimination function, because of the absence of an energy discrimination function, the detection accuracy may decline due to a difference in the composition of a foreign substance contained in the subject (for example, a difference of whether being bone or meat or whether being cartilage or a foreign substance in a meat inspection) and a difference in thickness. Therefore, it has been proposed to arrange in parallel two line sensors for detecting X-rays of different energy ranges, acquire a subtraction image being a difference data image from X-ray images detected by these two line sensors, and thereby improve the detection accuracy irrespective of the composition and thickness of a foreign substance contained in a subject (refer to, for example, Japanese Published Unexamined Patent Application H10-318943).

SUMMARY OF THE INVENTION

However, according to investigation by the inventors of the present invention, it has been found that an image part indicating a foreign substance etc., may have unclear edges in a subtraction image in an attempt to acquire a subtraction image from X-ray image of a subject detected and generated by two line sensors arranged in parallel. For this reason, detection of a foreign substance etc., contained in a subject cannot always be performed with accuracy by merely using two line sensors.

The present invention has therefore been made in view of such problems, and an object thereof is to provide a radiation detection device, a radiation image acquiring system, a radiation detection system, and a radiation detection method capable of improving the detection accuracy of a foreign substance etc., contained in a subject.

The inventors have devoted themselves to continuous study in order to attain the above-mentioned object, and found out that unclear edges of an image part indicating a foreign substance etc., in an energy subtraction image are caused mainly by the existence of a dead zone region sandwiched by the two line sensors. The dead zone region can indeed be reduced to the extent possible, but is inevitably generated when different pixels are provided on an identical chip. Then, the inventors completed the present invention upon obtaining the knowledge that the detection accuracy in a foreign substance inspection by two line sensors can be improved by performing adjustment of X-ray detection timing by two line sensors based on the width of the dead zone region.

More specifically, a radiation detection device according to the present invention, which is a radiation detection device that irradiates radiation to a subject from a radiation source, and detects radiation in a plurality of energy ranges transmitted through the subject, includes: a first detector for detecting radiation in a first energy range that is transmitted through the subject to generate first radiation image data; a second detector arranged in parallel to the first detector with a predetermined region sandwiched therebetween, for detecting radiation in a second energy range that is transmitted through the subject to generate second radiation image data; and a timing control section for controlling detection timing of at least the second detector, based on a width of the predetermined region, so that first radiation image data to be generated by the first detector and second radiation image data to be generated by the second detector mutually correspond.

Moreover, a radiation inspection method according to the present invention, which is a radiation inspection method in a radiation detection device including a radiation source for irradiating radiation to a subject, a first detector for detecting radiation in a first energy range, a second detector arranged in parallel to the first detector with a predetermined region sandwiched therebetween, for detecting radiation in a second energy range, and a timing control section for controlling detection timing of radiation in the first detector and the second detector, includes: an irradiation step of the radiation source irradiating radiation to the subject; a first detection step of the first detector detecting radiation in a first energy range irradiated in the irradiation step and transmitted through the subject to generate first radiation image data; a second detection step of the second detector detecting radiation in a second energy range irradiated in the irradiation step and transmitted through the subject to generate second radiation image data; and a timing control step of the timing control section controlling detection timing in at least the second detection step, based on a width of the predetermined region, so that first radiation image data to be generated by the first detection step and second radiation image data to be generated by the second detection step mutually correspond.

In the radiation detection device and the radiation inspection method, the timing control section, based on the width of the predetermined region, controls the detection timing of at least the second detector so that radiation image data to be generated by the first detector and radiation image data to be generated by the second detector mutually correspond. The detection timing in the second detector where a shift (delay etc.,) has occurred with respect to the detection timing in the first detector due to the existence of the predetermined region is thereby adjusted, so that radiation image data to be generated by the first detector and radiation image data to be generated by the second detector mutually correspond. And, in a subtraction image that is acquired from mutually corresponding two sets of radiation image data, an unclear edge part is reduced. As a result, the detection accuracy of a foreign substance etc., contained in the subject can be improved.

Moreover, when generating a subtraction image, an unclear edge part can be generally reduced by image processing. However, in an attempt to reduce an unclear edge part by image processing when detecting a foreign substance contained in a subject to be conveyed at a high speed (for example, 80 m per minute), the image processing speed may not easily respond to the high conveying speed. To cope therewith, according to the radiation detection device and the radiation inspection method mentioned above, the detection timing of a radiation image is controlled to reduce an unclear edge part from a subtraction image, and thus a subtraction image with a reduced clear edge part can be speedily generated even when the conveying speed of the subject is a high speed. As a result, even in a high-speed foreign substance inspection, the detection accuracy of a foreign substance etc., contained in the subject can be improved.

It is preferable that the first detector is a first line sensor that generates the first radiation image data in successive divided image data, the second detector is a second line sensor that generates the second radiation image data in successive divided image data, and the timing control section controls to delay detection timing of at least the second line sensor based on a width of the predetermined region so that a detection range in the subject of divided image data by the first line sensor and a detection range in the subject of divided image data by the second line sensor are coincident. By thus controlling to delay the detection timing of the second line sensor so that the detection ranges of the subject indicated by the divided image data are equalized, an unclear edge part in a subtraction image can be reliably reduced.

It is preferable that the width of the predetermined region is a width along a short-side direction of the first detector or the second detector and smaller than a sensing width to sense radiation in the first detector or the second detector. The width of the predetermined region being narrow allows preventing geometric blur in a subtraction image based on a radiation image to be generated by the first detector or the second detector.

A radiation image acquiring system according to the present invention may include: the aforementioned radiation detection device; and a timing calculating section for calculating the detection timing based on the width of the predetermined region. The timing control section, by using the detection timing calculated by the timing calculating section, can control detection timing etc., of the second detector to generate a subtraction image with a reduced unclear edge part.

The radiation image acquiring system may include a composite image generating section for generating a composite image by synthesizing radiation image data generated by the first detector and radiation image data generated by the second detector while being controlled by the timing control section so as to mutually correspond. Such a composite image generating section allows acquiring a subtraction image with a reduced unclear edge part.

A radiation inspection system according to the present invention, which is a radiation inspection system that irradiates radiation to a subject from a radiation source, and detects radiation in a plurality of energy ranges transmitted through the subject to inspect the subject, includes: a radiation irradiator for irradiating, as the radiation source, radiation to the subject; a first detector for detecting radiation in a first energy range that is transmitted through the subject to generate first radiation image data; a second detector arranged in parallel to the first detector with a predetermined region sandwiched therebetween, for detecting radiation in a second energy range that is transmitted through the subject to generate second radiation image data; a conveying section for conveying the subject in a direction perpendicular to an irradiation direction of the radiation by the radiation irradiator; a timing control section for controlling detection timing of at least the second detector, based on a width of the predetermined region and a conveying speed of the subject by the conveying section, so that first radiation image data to be generated by the first detector and second radiation image data to be generated by the second detector mutually correspond when detecting radiation transmitted through the subject that is conveyed by the conveying section by the first radiator and the second radiator; a composite image generating section for generating a composite image by synthesizing first radiation image data generated by the first detector and second radiation image data generated by the second detector while being controlled by the timing control section so as to mutually correspond; and a composite image output section for outputting the composite image generated by the composite image generating section. Such a radiation inspection system allows performing detection of a foreign substance contained in the subject and a baggage inspection etc., with accuracy.

It is preferable that the timing control section controls detection timing of at least the second detector, based on a magnification ratio being a ratio of a distance between the radiation irradiator and the subject to a distance between the radiation irradiator and the first detector or the second detector, besides the width of the predetermined region and the conveying speed mentioned above. Performing control including the magnification ratio allows performing detection of a foreign substance contained in the subject and a baggage inspection etc., with greater accuracy,

BRIEF DESCRIPTION OF THE DRAWINGS

FIG. 9(a) is a view showing a region to be detected by a low-energy detector, and FIG. 9(b) is a view showing a region to be detected by a high-energy detector, each showing an irradiating region when a subject S has a thickness.

DESCRIPTION OF THE PREFERRED EMBODIMENTS

Figure 1:
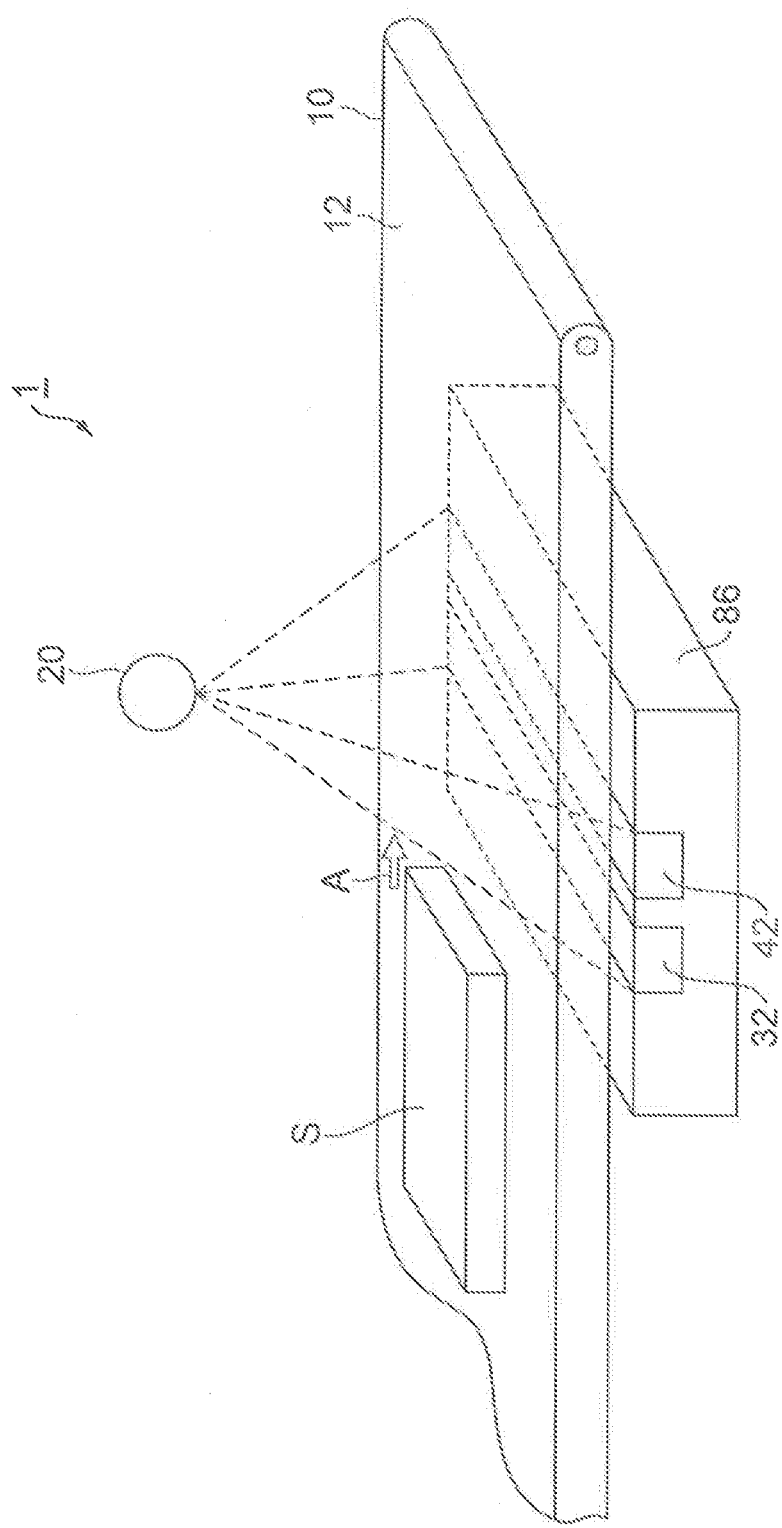
FIG. 1 is a perspective view of an X-ray image acquiring system according to the present embodiment.

Hereinafter, a preferred embodiment of an X-ray image acquiring system according to the present invention will be described with reference to the drawings. Also, the same or corresponding parts are denoted with the same reference numerals in description of the drawings, and overlapping description will be omitted.

Figure 2:
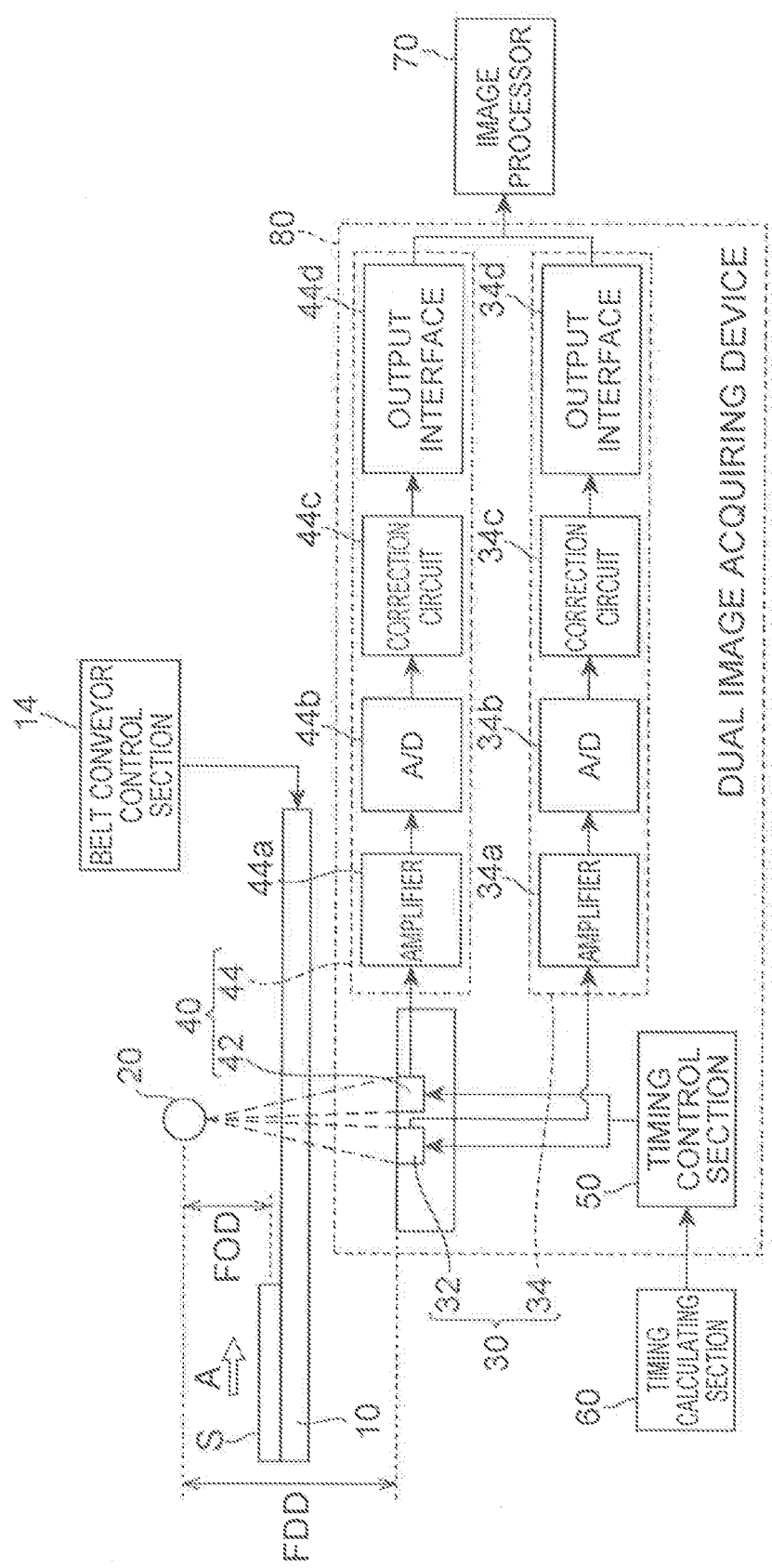
FIG. 2 is a schematic configuration diagram of the X-ray image acquiring system according to the present embodiment.

FIG. 1 is a perspective view of an X-ray image acquiring system according to the present embodiment, and FIG. 2 is a schematic configuration diagram of the X-ray image acquiring system according to the present embodiment. As shown in FIG. 1 and FIG. 2, the X-ray image acquiring system (radiation image acquiring system, radiation inspection system) 1 is an apparatus that irradiates X-rays (radiation) from an X-ray source (radiation source) to a subject S, and detects, of the irradiated X-rays, transmitted X-rays having been transmitted through the subject S in a plurality of energy ranges. The X-ray image acquiring system 1 carries out, by using a transmission X-ray image, detection of a foreign substance contained in the subject S and a baggage inspection etc. The X-ray image acquiring system 1 thus configured includes a belt conveyor (conveying section) 10, an X-ray irradiator (radiation irradiator) 20, a low-energy image acquiring section 30, a high-energy image acquiring section 40, a timing control section 50, a timing calculating section 60, and an image processor (composite image generating section, composite image output section) 70. The low-energy image acquiring section 30, the high-energy image acquiring section 40, and the timing control section 50 compose a dual image acquiring device (radiation detection device) 80.

The belt conveyor 10, as shown in FIG. 1, includes a belt portion 12 on which the subject S is placed. The belt conveyor 10 makes the belt portion 12 move in a conveying direction A (from an upstream side at the left-hand side of FIG. 1 to a downstream side at the right-hand side of FIG. 1) to thereby convey the subject S in the conveying direction A at a predetermined conveying speed. The conveying speed of the subject S is, for example, 48 m/minute. The belt conveyor 10 can, if necessary, be changed in speed by a belt conveyor control section 14 to a conveying speed of, for example, 24 m/minute or 96 m/minute. Moreover, the belt conveyor control section 14 can change the height position of the belt portion 12. Changing the height position of the belt portion 12 allows changing a distance between the X-ray irradiator 20 and the subject S (equal to "FOD" to be described later). This change makes it possible to change the resolution of an X-ray transmission image to be obtained by the low-energy image acquiring section 30 and the high-energy image acquiring section 40. Here, examples of the subject S to be conveyed by the belt conveyor 10 broadly include resource materials such as minerals, waste products for segregation and resource recovery (recycling), and electronic components, besides food such as edible meat, rubber products such as tires, baggage and cargo subjected to inspection for the sake of security and safety.

The X-ray irradiator 20 is a device that irradiates X-rays to the subject S as an X-ray source. The X-ray irradiator 20 is a point source, which irradiates while dimming X-rays at a predetermined angular range in a fixed irradiation direction. The X-ray irradiator 20 is arranged above the belt portion 12 at a predetermined distance from the belt portion 12 so that the direction of X-ray irradiation is oriented to the belt portion 12 and the diffusing X-rays extend in the entire width direction (direction perpendicular to the conveying direction A) of the subject S. Moreover, the X-ray irradiator 20, in a length direction (direction parallel to the conveying direction A) of the subject 5, has a predetermined divided range in the length direction as its irradiation range, and is structured so that X-rays are irradiated to the subject S across the length direction thereof as a result of the subject S being conveyed by the belt conveyor 10 in the conveying direction A.

The low-energy image acquiring section 30 includes a low-energy detector (first detector) 32 and a low-energy image correcting section 34.

The low-energy detector 32 detects, of the X-rays irradiated from the X-ray irradiator 20, X-rays in a low-energy range (first energy range) having been transmitted through the subject S to generate low-energy image data (first radiation image data). The low-energy detector 32 is formed of, for example, a linear line sensor with a length equal to or more than the width of the subject S, and arranged below an upstream side of the belt portion 12 so as to be perpendicular to the conveying direction A with an X-ray detection plane thereof opposed to the X-ray irradiator 20.

The low-energy image correcting section 34 is a part that amplifies and corrects the low-energy image data generated by the low-energy detector 32. The low-energy image correcting section 34 includes an amplifier 34a that amplifies low-energy image data, an A/D converter 34b that A/D-converts the low-energy image data amplified by the amplifier 34a, a correction circuit 34c that carries out a predetermined correction processing for the low-energy image data converted by the A/D converter 34b, and an output interface 34d that externally outputs the image data corrected by the correction circuit 34c.

The high-energy image acquiring section 40 includes a high-energy detector (second detector) 42 and a high-energy image correcting section 44.

The high-energy detector 42 detects, of the X-rays irradiated from the X-ray irradiator 20, X-rays in a high-energy range (second energy range) having been transmitted through the subject S to generate high-energy image data (second radiation image data). The high-energy detector 42 is formed of, for example, a linear line sensor with a length equal to or more than the width of the subject S, and arranged below a downstream side of the belt portion 12 so as to be perpendicular to the conveying direction A with an X-ray detection plane thereof opposed to the X-ray detector 20. However, the low-energy range in which X-rays are detected by the low-energy detector 32 and the high-energy range in which X-rays are detected by the high-energy detector 42 are not clearly distinguished, and the energy ranges are overlapped with each other to some extent.

The high-energy image correcting section 44 is a part that amplifies and corrects the high-energy image data generated by the high-energy detector 42. The high-energy image correcting section 44 includes an amplifier 44a that amplifies high-energy image data, an A/D converter 44b that A/D-converts the high-energy image data amplified by the amplifier 44a, a correction circuit 44c that carries out a predetermined correction processing for the high-energy image data converted by the A/D converter 44b, and an output interface 44d that externally outputs the image data corrected by the correction circuit 44c.

Figure 3:
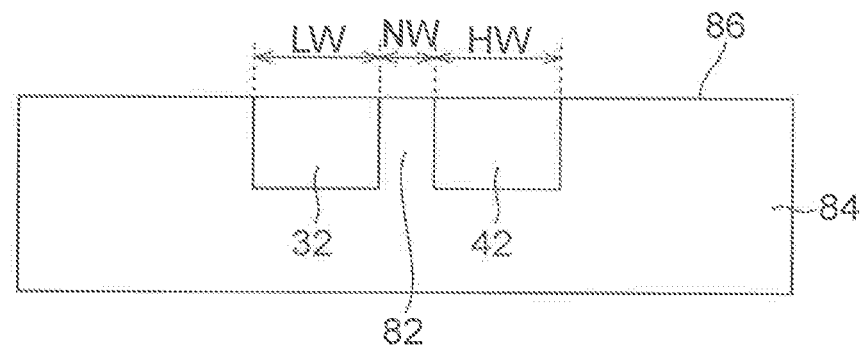
FIG. 3 is a side view of a dual energy sensor according to the present embodiment.

Here, the low-energy detector 32 and the high-energy detector 42 will be described in detail. As shown in FIG. 1 and FIG. 3, the low-energy detector 32 is a line sensor with a sensing width of LW along the conveying direction. A. In addition, the high-energy detector 42 is a line sensor with a sensing width of HW along the conveying direction. A. The sensing width of LW and the sensing width of HW, in the present embodiment, are the same width, and for example, 0.8 mm. Moreover, the low-energy detector 32 having the sensing width LW and the high-energy detector 42 having the sensing width HW thus configured are arranged and fixed onto a base 84 in parallel with a dead zone region (predetermined region) 82 having a dead zone width NW sandwiched therebetween along the convening direction A, that is, a short-side direction of each detector being a line sensor, and compose a dual energy sensor 86, which is a semiconductor detector, In the dual energy sensor 86, in order to minimize a parallax between a low-energy image and a high-energy image (difference in the path of X-rays incident from the X-ray source), the distance between both detectors 32, 42 is set to be as narrow as possible. Therefore, the dead zone width NW of the dead zone region 82 is set to be as narrow as possible with such a minimum thickness as to prevent electrons in each detector 32, 42 from flowing into the other detector. Such a dead zone width NW is, in the present embodiment, for example, 0.4 mm, which is narrower than the sensing width LW, HW (0.8 mm) of each detector 32, 42.

In addition, as the low-energy detector 32 and the high-energy detector 42 to compose the dual energy sensor 86, for example, one with an energy discrimination function for which a low-energy cutting filter is arranged on a high-energy sensor may be used. Alternatively; a scintillator for converting X-rays in a low-energy range to visible light and a scintillator for converting X-rays in a high-energy range to visible light may be used to provide both detectors 32, 42 with different wavelength sensitivities, so as to allow detecting different energy ranges. In addition, filters may be arranged on scintillators having different wavelength sensitivities. Further, there may be one with an energy discrimination function by a direct conversion method of CdTe (cadmium telluride) or the like.

Figure 7:
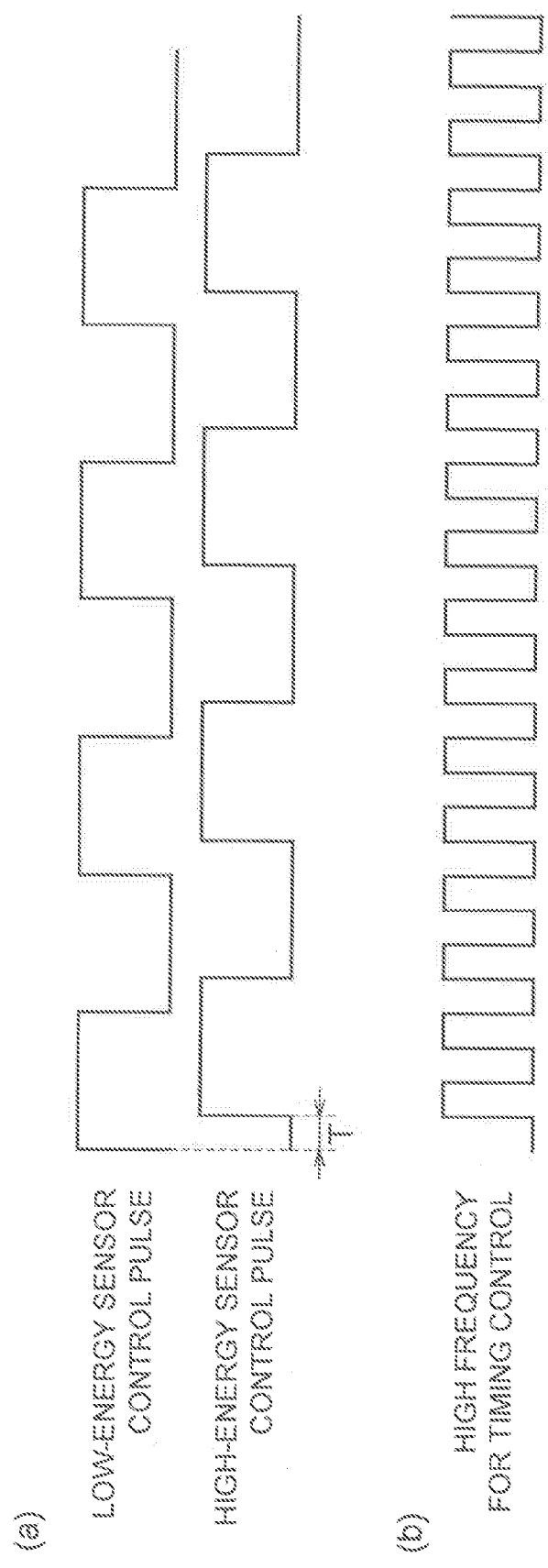
FIG. 7(a) is a diagram showing a control pulse signal of each detector in the X-ray image acquiring system according to the present embodiment.
FIG. 7(b) is a high-frequency signal for generating a control pulse signal.

The timing control section 50 controls the detection timing of transmitted X-rays in the low-energy detector 32 and the detection timing of transmitted X-rays in the high-energy detector 42. The timing control section 50, to the low-energy detector 32, outputs low-energy sensor control pulses of a predetermined frequency as shown in FIG. 7(*a*). Moreover, the timing control section 50, to the high-energy detector 42, outputs a high-energy sensor control pulse signal of the same frequency as that of low-energy sensor control pulses and delayed in the rising spot of pulses by a predetermined time T (hereinafter, sometimes referred to as a "delay time T"). When such control pulses are input, each detector 32, 42 outputs, as image data, transmitted X-rays received on a one-cycle basis of each control pulse every time each cycle ends.

Figure 5:
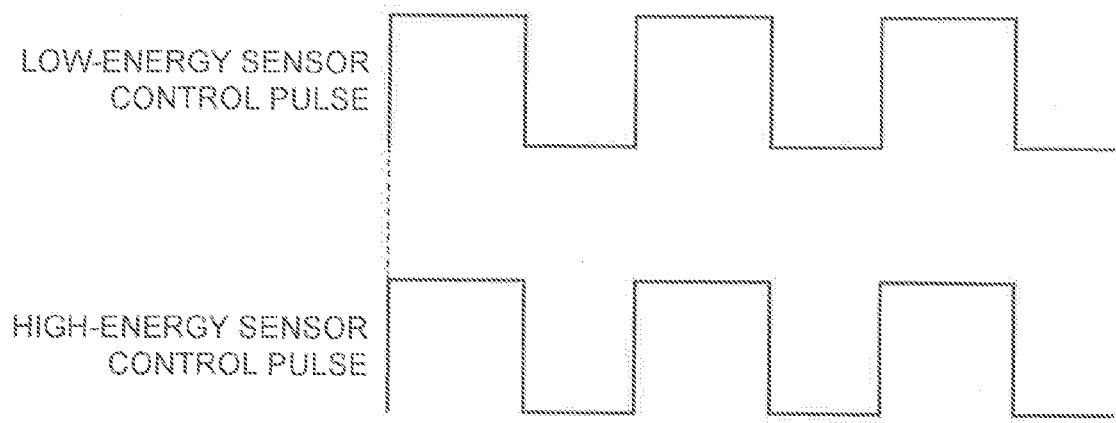
FIG. 5 is a diagram showing a control pulse signal of each detector in an X-ray image acquiring system according to a comparative example.

The delay time T is equivalent to an image mismatch that is generated between low-energy image data to be detected and generated by the low-energy detector 32 and high-energy image data to be detected and generated by the high-energy detector 42 when a control pulse signal of a predetermined frequency as shown in FIG. 5 is input simultaneously to the low-energy detector 32 and the high-energy detector 42. More specifically, the delay time T is an adjustment time that is determined from the dead zone width NW of the dead zone region 82 in the dual energy sensor 86, speed at which the subject S passes through the dead zone region 82 (that is, the conveying speed M), etc.

When the timing control section 50 generates the control pulse signal including the delay time T, a PLL (Phase Locked Loop) or the like is used to generate a high frequency signal for timing control shown in FIG. 7(*b*). As such a high-frequency signal, for example, in the case of driving at a pixel clock required for sensor drive of about 200 kHz in the energy detector 32, 42 or the like, using a signal of a frequency of 20 MHz or more about 100 times that frequency allows meticulous control. In the case of a pixel clock for sensor drive of about 1 MHz, using likewise a signal of 100 MHz or more allows meticulous control. The higher the frequency of a high-frequency signal, the more flexibly a change in conveying speed M, pixel clock, or the like can be responded to, and thus meticulous control can be performed. In addition, a high-frequency oscillator for a delay signal may be used, in place of the PLL, to generate a delay control pulse signal.

The timing control section 50 generates the control pulse signal including the delay time T from such a high-frequency signal generated by using a PLL or the like. Then, the timing control section 50 controls the timing for detecting transmitted X-rays in the low-energy detector 32 and the high-energy detector 42 based on the delay time T so that the low-energy image data and the high-energy image data respectively correspond to thereby reduce the image mismatch.

The timing calculating section 60 calculates a delay time T, which is a detection timing to be used by the timing control section 50. The timing calculating section 60 calculates the delay time T by the following formula (1) based on the dead zone width NW of the dead zone region 82 in the dual energy sensor 86 and speed at which the subject S passes through the dead zone region 82 (that is, the conveying speed M). Although description will be given in the present embodiment of an example of the case where FOD (Focus Object Distance) shown in FIG. 2 and FDD (Focus Detector Distance) being a distance between the X-ray irradiator 20 and each detector 32, 42 are equal to each other, and thus an X-ray transmission image is not magnified (that is, when the magnification ratio R is 1) for ease in description, the magnification ratio R is not limited thereto:

$$T = NW/M \quad (1)$$

The delay time T in the detection timing of the high-energy detector 42 relative to the detection timing of the low-energy detector 32 is calculated by the formula (1). Then, the timing calculating section 60 outputs the calculated delay time T to the timing control section 50 as detection timing. In addition, the dead zone width NW and the conveying speed M are input to the timing calculating section 60 via an input section or the like.

The image processor 70 is a device that performs an arithmetic processing for obtaining difference data between the low-energy image data detected and generated by the low-energy detector 32 and the high-energy image data detected and generated by the high-energy detector 42, and generates an energy subtraction image, which is a composite image. Both energy image data to be input to the image processor 70 have been controlled in terms of detection timing, by the timing control section 50, so that mutual image data correspond. The image processor 70 outputs to display the energy subtraction image generated by the arithmetic processing on a display or the like. This output display allows visually confirming a foreign substance contained in the subject S. In addition, without outputting to display an energy subtraction image, only data output may be performed so as to detect a foreign substance etc., contained in the subject S directly from image data by a detection processing in the image data.

Figure 4:
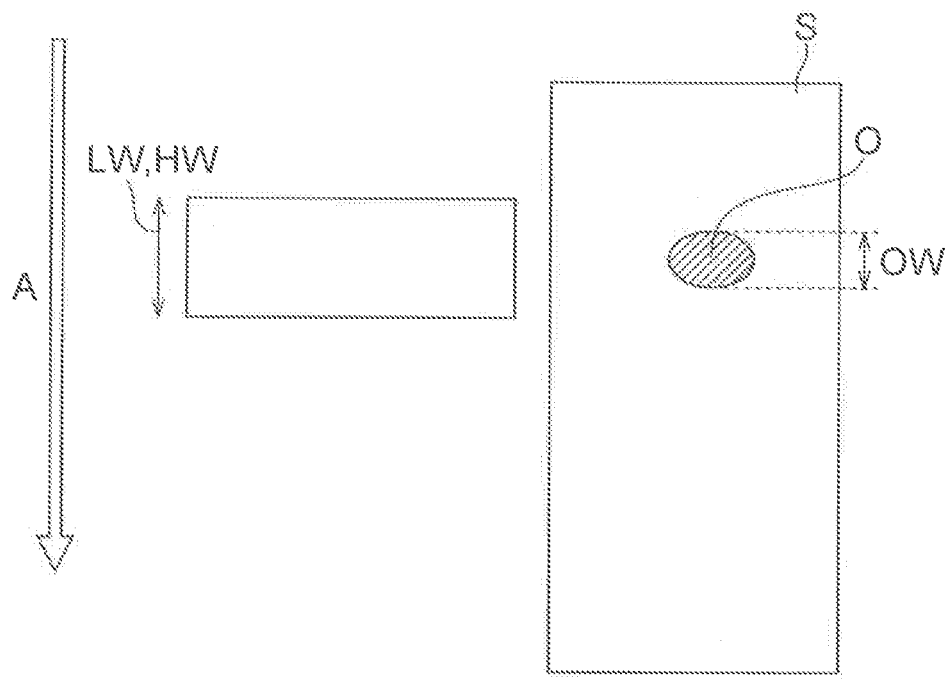
FIG. 4 is a view showing a subject containing a foreign substance.

Here, a calculation method of the delay time T in detection timing to be used by the timing control section 50 and actions will be described by taking an example of acquiring a transmission X-ray image of a subject S (refer to FIG. 4) and detecting a foreign substance O contained in the subject S. The subject S to be used for the description is supposed to be one having a length of 4.0 mm in a direction along the conveying direction A and containing a foreign substance O (having a length OW of 0.6 mm) smaller than the sensing width LW, HW (hereinafter, referred to also as a "pixel pitch") of each detector 32, 42 in a predetermined position. The sensing width LW, HW of each detector 32, 42 is 0.8 mm, and for acquiring a shape without geometric contraction of the entire subject S having a length of 4.0 mm, that is, a transmission X-ray image for inspection of a length of not more than 0.8 mm at a detection width of 0.8 mm, five or more sets of divided image data are respectively required. Moreover, it is supposed that the conveying speed of the belt conveyor 10 is 0.8 mm/millisecond (48 m/minute). In addition, it is supposed for ease in description that the thickness of the subject S is so thin as not to cause blur due to the thickness, and as described above, FOD and FDD shown in FIG. 2 are equal to each other, and thus an X-ray transmission image is not magnified (having a magnification ratio R of 1).

Figure 6:
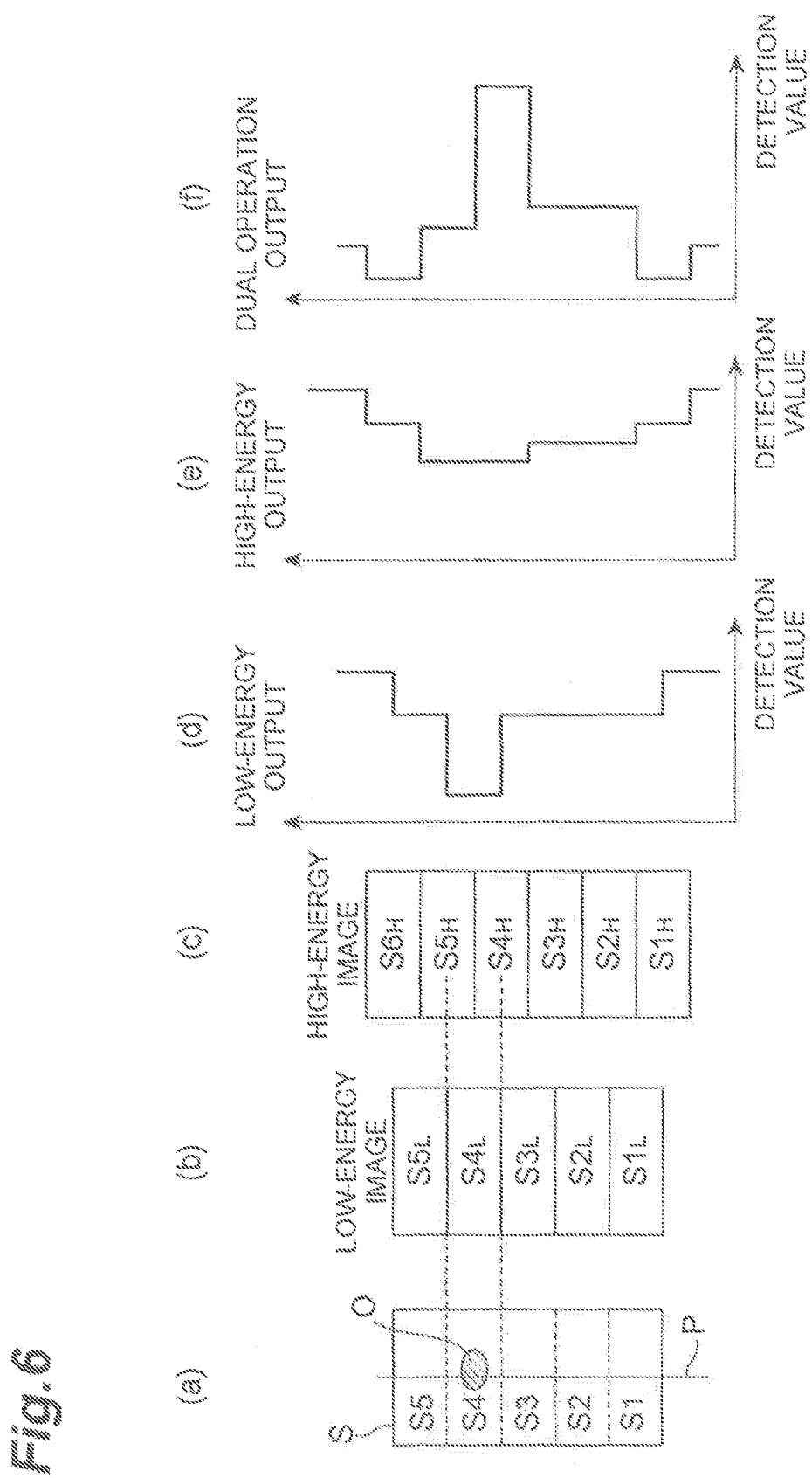
FIG. 6 are diagrams each showing an energy sensor image or an energy output to be generated by the X-ray image acquiring system according to the comparative example.

First, description will be given of a case, as a comparative example, of acquiring a radiation image of the subject S without using the delay time T in detection timing, by using FIG. 5 and FIG. 6. In this case, for acquiring an X-ray image of the subject S to be conveyed in the conveying direction A at a conveying speed of 0.8 mm/millisecond, the timing control section 50, as shown in FIG. 5, outputs control pulses of the same frequency that are the same in the detection timing of the low-energy detector 32 and the high-energy detector 42 simultaneously to the low-energy detector 32 and the high-energy detector 42 to acquire divided image data for every 0.8 mm in each detector 32, 42.

A low-energy output by pixels of the low-energy detector 32 corresponding to a line P of FIG. 6(a) is shown in FIG. 6(d). Likewise, a high-energy output by pixels of the high-energy detector 42 corresponding to the line P of FIG. 6(a) is shown in FIG. 6(e). When a first divided range S1 (first 0.8 mm equivalent) located at the front of the subject S passes over a detection plane, which is an imaging region of the low-energy detector 32, the low-energy detector 32 images the first divided range S1 of the subject S in the low-energy range to, as shown in FIG. 6(b), first generate first divided image data $S1_L$. The subject S thereafter moves at a conveying speed of 0.8 mm/millisecond, and after one millisecond, of the first divided range S1 of the subject S, a part corresponding to leading 0.4 mm is located over a detection plane, which is an imaging region of the high-energy detector 42, and a part corresponding to remaining 0.4 mm is located over the dead zone region 82. In the comparative example, X-ray detection in both energy detectors 32, 42 is controlled by equally-timed control pulses, and thus: as described above, while a part of the subject S is located over the dead zone region 82, the high-energy detector 42 generates first divided image data. $S1_H$ corresponding to the first divided range S1 (first divided image data $S1_L$) of the subject S. In addition, simultaneously with the high-energy detector 42 generating the first divided image data $S1_H$, the low-energy detector 32 generates second divided image data $S2_L$ in a second divided range 82 following the first divided range S1.

Between the first divided image data $S1_L$ generated by the low-energy detector 32 and the first divided image data $S1_H$ generated by the high-energy detector 42, a mismatch is generated based on the dead zone width NW of the dead zone region 82 and the speed at which the subject S moves through that dead zone region (that is, the conveying speed M). Then, while maintaining the mismatch, the low-energy detector 32 and the high-energy detector 42 that are controlled by control pulse signals output simultaneously at the same frequency successively detect transmitted X-rays to generate remaining divided image data. As a result, the low-energy detector 32 that detects transmitted X-rays from the subject S in the low-energy range generates divided image data (five sets of divided image data of $S1_L$, $S2_L$, $S3_L$, $S4_L$, and $S5_L$) for a low-energy image as shown in FIG. 6(b). On the other hand, the high-energy detector 42 that detects transmitted X-rays from the subject S in the high-energy range generates divided image data (six sets of divided image data of $S1_H$, $S2_H$, $S3_H$, $S4_H$, $S5_H$, and $S6_H$) for a high-energy image as shown in FIG. 6(c).

Here, comparing the divided image data shown in FIG. 6(b) and the divided image data shown in FIG. 6(c) indicates that there is no correspondence obtained between both divided image data by reference to the subject S, due to the mismatch based on the dead zone width NW and the conveying speed M. Therefore, for example, a site where data on a foreign substance O part is most contained is one set of image data, such as divided image data $S4_L$, in a low-energy image by the low-energy detector 32, whereas in a high-energy image by the high-energy detector 42, as shown in FIG. 6(c), the site is across two sets of divided image data of divided image data $S4_H$ and $S5_H$. In addition, a low-energy output corresponding to the low-energy image, as shown in FIG. 6(d), is remarkably changed in detection value in only one pixel pitch corresponding to the divided image data $S4_L$ to indicate a position where the foreign substance O is contained, whereas a high-energy output corresponding to the high-energy image, as shown in FIG. 6(e), is slightly changed in detection value (for example, about a half of the change in detection value of the low-energy output) in two pixel pitches corresponding to the divided image data $S4_H$ and $S5_H$ to roughly indicate a position where the foreign substance O is contained. As a result, the site and amount of change in direction value are different between both energy outputs.

The image processor 70, in an attempt to acquire a subtraction image based on the detection value data (refer to FIGS. 6(d) and (e)) different in the site and amount of change in detection value as such, as a result of the site and amount of change in detection value due to the foreign subject O becoming unclear, can no longer acquire a subtraction image where the position of the foreign substance O in the subject S is shown with accuracy. Moreover, because the divided image data corresponding to each detection value data are respectively mismatched, a rising part in brightness of each edge part shown in FIG. 6(f) is also blurred. As a result, it becomes even more difficult to obtain a subtraction image where the position of the foreign substance O in the subject S is shown with accuracy. As such, without controlling the detection timing in the low-energy detector 32 and the detection timing in the high-energy detector 42 with accuracy, the detection accuracy of a foreign substance may decline due to the mismatch and blur as described above.

Figure 8:
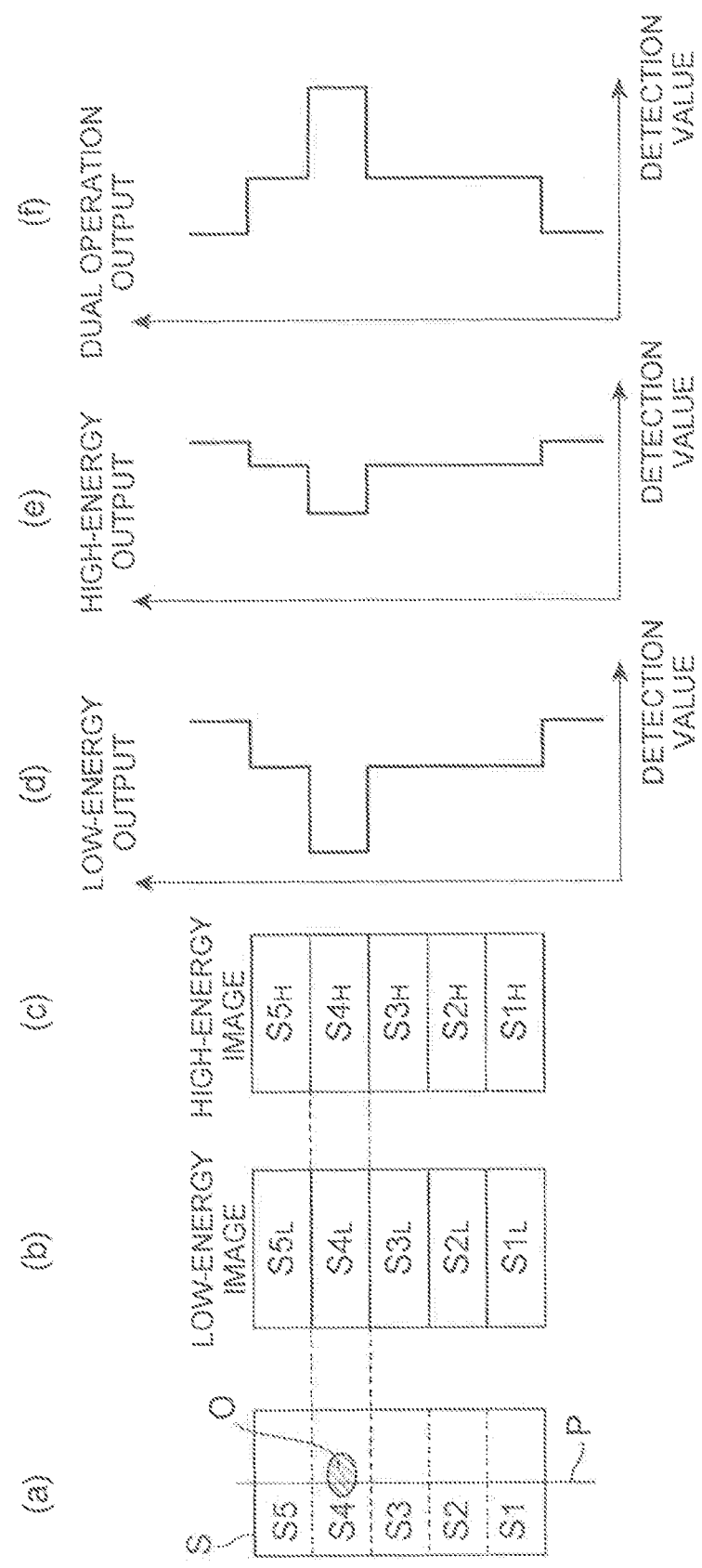
FIG. 8 are diagrams each showing an energy sensor image or an energy output to be generated by the X-ray image acquiring system according to the present embodiment.

Next, description will be given of a case of acquiring a low-energy image and a high-energy image of the subject S using the delay time T in detection timing so that both energy images correspond, in order to prevent such generation of mismatch and blur, by using FIG. 7 and FIG. 8.

In this case, for acquiring an X-ray image of the subject S to be conveyed in the conveying direction A at a conveying speed of 0.8 mm/millisecond, the timing control section 50, as shown in FIG. 7, outputs control pulses of the same frequency, where the detection timing of the high-energy detector 42 is delayed by the predetermined time T with respect to the detection timing of the low-energy detector 32, to the low-energy detector 32 and the high-energy detector 42 to acquire divided image data for every 0.8 mm in each detector 32, 42.

More specifically, when the first divided range S1 (first 0.8 mm equivalent) at the front of the subject S passes over a detection plane, which is an imaging region of the low-energy detector 32, the low-energy detector 32 images the first divided range S1 of the subject S in the low-energy range to, as shown in FIG. 8(b), first generate first divided image data S1$_L$. The subject S thereafter moves at a conveying speed of 0.8 mm/millisecond, and after one millisecond, of the first divided range S1 of the subject S, a part corresponding to leading 0.4 mm is located over a detection plane, which is an imaging region of the high-energy detector 42, and a part corresponding to remaining 0.4 mm is located over the dead zone region 82. In the present embodiment using the delay time T, X-ray detection in the high-energy detector 42 is delayed by a time until moving the subject S another 0.4 mm so that the predetermined divided position at the front of the subject S is not located over the dead zone region 82. The delay time T, on the conditions described above, is calculated as 0.5 milliseconds from the formula (1).

The high-energy detector 42 acquires the first divided image data S1$_H$ corresponding to the first divided range S1 of the subject S, due to the high-energy sensor control pulse signal with the delay time T provided as 0.5 milliseconds, when the first divided range S1 of the subject S has passed the dead zone region 82, that is, the entire first divided range S1 of the subject S has reached over the detection plane of the high-energy detector 42. In addition, before the high-energy detector 42 generates the first divided image data S1$_H$ (before the delay time T elapses), the low-energy detector 32 generates the second divided image data S2$_L$ following the first divided image data S1$_L$.

Between the first divided image data S1$_L$ generated by the low-energy detector 32 and the first divided image data S1$_H$ generated by the high-energy detector 42, there is no mismatch based on the dead zone width NW of the dead zone region 82 and the speed at which the subject S moves through that dead zone region 82 (that is, the conveying speed M), and as shown in FIGS. 8(b) and (c), both image data correspond. Then, while both image data remain corresponding, the low-energy detector 32 and the high-energy detector 42 that are controlled by control pulse signals output at the same frequency in consideration of the delay time T based on the dead zone width NW etc., successively detect transmitted X-rays to generate remaining divided image data. As a result, the low-energy detector 32 that detects transmitted X-rays from the subject S in the low-energy range generates divided image data (five sets of divided image data of S1$_L$, S2$_L$, S3$_L$, S4$_L$, and S5$_L$) for a low-energy image as shown in FIG. 8(b), while the high-energy detector 42 that detects transmitted X-rays from the subject S in the high-energy range generates divided image data (five sets of divided image data of S1$_H$, S2$_H$, S3$_H$, S4$_H$, and S5$_H$) for a high-energy image as shown in FIG. 8(c). In addition, both image data respectively correspond in the image ranges of the subject S.

Here, comparing the divided image data shown in FIG. 8(b) and the divided image data shown in FIG. 8(c) indicates that there is correspondence obtained between both divided image data by reference to the subject S, due to the delay time T based on the dead zone width NW and the conveying speed M. Therefore, for example, a site where data on a foreign substance O part is most contained is one set of image data, such as divided image data S4$_L$, in a low-energy image by the low-energy detector 32, and also in a high-energy image by the high-energy detector 42, the site is one set of image data, such as divided image data S4$_H$. In addition, a low-energy output corresponding to the low-energy image, as shown in FIG. 8(d), is remarkably changed in detection value in only one pixel pitch corresponding to the divided image data S4$_L$ to indicate a position where the foreign substance O is contained, and a high-energy output corresponding to the high-energy image, as shown in FIG. 8(e), is also remarkably changed in detection value in only one pixel pitch corresponding to the divided image data S4$_H$ to indicate a position where the foreign substance O is contained. As a result, the site and amount of change in direction value are coincident between both energy outputs. However, the foreign substance O does not need to be always contained in one divided image, and it suffices that a divided image where the foreign substance O is contained in a low-energy image and a divided image where the foreign substance O is contained in a high-energy image are coincident.

The image processor 70, in an attempt to acquire a subtraction image based on the detection value data (refer to FIGS. 8(d) and (e)) coincident in the site and amount of change in detection value as such, as a result of the site and amount of change in detection value due to the foreign subject O becoming clear, can acquire a subtraction image where the position of the foreign substance O in the subject S is shown with accuracy. Moreover, because the divided image data corresponding to each detection value data respectively correspond, a rising, part in brightness of each edge part shown in FIG. 8(f) also becomes distinct. As a result, a subtraction image where the position of the foreign substance O in the subject S is shown with greater accuracy can be acquired. As such, as a result of the detection timing in the low-energy detector 32 and the detection timing in the high-energy detector 42 being controlled with accuracy due to the delay time T based on the dead zone width NW and the conveying speed M, decline in detection accuracy of a foreign substance due to the mismatch and blur as described above can be prevented, so that it becomes possible to detect a foreign substance with accuracy.

As has been described above, in the X-ray image acquiring system 1, the timing control section 50, based on the dead zone width NW of the dead zone region 82 and the conveying speed M, controls to delay the detection timing of at least the high-energy detector 42 so that low-energy image data to be generated by the low-energy detector 32 and high-energy image data to be generated by the high-energy detector 42 mutually correspond. The detection timing in the high-energy detector 42 where a shift (delay etc.,) has occurred with respect to the detection timing in the low-energy detector 32 due to the existence of the dead zone region 82 is thereby adjusted, so that low-energy image data to be generated by the low-energy detector 32 and high-energy image data to be generated by the high-energy detector 42 mutually correspond. And, in a subtraction image that is acquired from mutually corresponding two sets of energy image data, changes in detection value indicating a foreign substance become clear, and an unclear edge part is reduced. As a result, the detection accuracy of a foreign substance O etc., contained in the subject S can be improved.

Moreover, in the above-mentioned embodiment, provided is the timing calculating section 60 for calculating detection timing based on the dead zone width NW and the conveying speed M. The timing control section 50, by using the detection timing calculated by the timing calculating section 60, can control detection timing etc., of the low-energy detector to generate a subtraction image with a reduced unclear edge part.

The low-energy detector 32 is a line sensor that generates low-energy image data in successive divided image data, the high-energy detector 42 is A line sensor that generates high-energy image data in successive divided image data, and the timing control section 50 is structured so as to control to delay the detection timing of at least the line sensor of the high-energy detector 42 based on the dead zone width NW and the conveying speed M so that a detection range in the subject S indicated in divided image data by a line sensor according to the low-energy detector 32 and a detection range in the subject S indicated in divided image data by a line sensor according to the high-energy detector 42 are coincident. By thus controlling to delay the detection timing of the line sensor of the high-energy detector 42 so that the detection ranges of the subject S indicated by the divided image data are coincident, in a subtraction image, changes in detection value indicating a foreign substance become clear, and an unclear edge part is reduced.

Although a preferred embodiment of the present invention has been described in the above, the present invention is by no means limited to the above-mentioned embodiment, and various modifications can be made. For example, in the above-mentioned embodiment, a description has been given in the case where FOD and FDD shown in FIG. 2 are equal to each other, and thus an X-ray transmission image is not magnified, however, the present invention can also be applied to a case where FOD and FDD are different from each other to cause magnification. The magnification ratio R is 2 times when, for example, FOD:FDD=1:2, and an X-ray transmission image is also magnified 2 times. If, for example, the conveying speed M is 0.4 mm/millisecond, an image in each detector 32, 42 is projected at a speed equal to 0.8 mm/millisecond. The delay time T in consideration of such a magnification ratio is calculated by using the following formula (2) in place of the formula (1).

$$T=NW/(M\times R) \quad (2)$$

In addition, the magnification ratio R is input to the timing calculating section 60 from a storage device (not shown) or the like in the X-ray image acquiring system 1.

Figure 10:
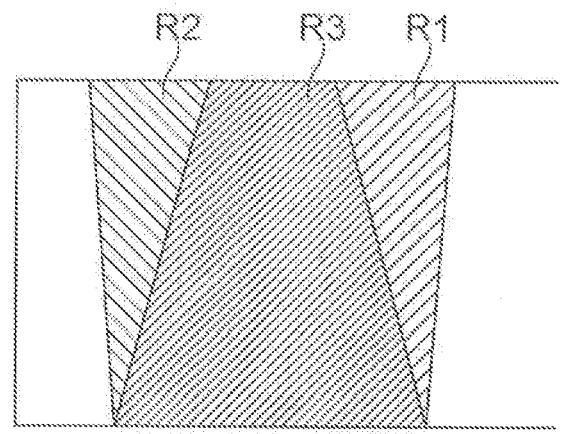
FIG. 10 is a view showing a state where the detecting regions shown in FIG. 9, are coincident.

Moreover, in the above-mentioned embodiment, although a description has been given assuming that the subject S has virtually no thickness, the present invention can also be applied to a case where the subject S has a predetermined thickness, for example, as shown in FIG. 9. In this case, FOD is calculated with reference to the height of a bottom surface part of the subject S to determine a magnification ratio R, and the delay time T is calculated by the formula (2) or the like. Then, the subject S is conveyed by the belt conveyor 10 as in the above-mentioned embodiment to, as shown in FIG. 9(*a*), first detect a low-energy image in the region R1 of the subject S by the low-energy detector 32 and generate low-energy image data. The subject S thereafter moves in the conveying direction A according to the delay time T to, as shown in FIG. 9(*b*), detect a high-energy image in the region R2 of the subject S by the high-energy detector 42 and generate high-energy image data. The region R1 and the region R2 are substantially coincident in a lower irradiation plane R1*a*, R2*a* of an illustrated lower surface of the subject S, and the low-energy image in the region R1 and the high-energy image in the region R2, as shown in FIG. 10, include X-ray transmission data of a part corresponding to a shared region R3. The larger the shared region R3, the less mismatch is generated between both energy images, so that the detection accuracy of the foreign substance O contained in the subject S can be improved.

Figure 11:
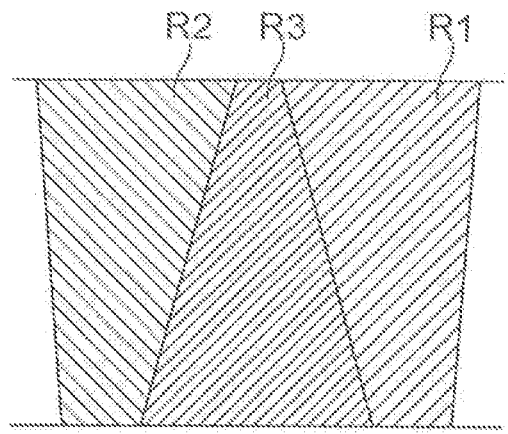
FIG. 11 is a view showing a state where the detecting regions shown in FIG. 9 are not coincident.

Description will be given, as a case where the subject S has a thickness as such, of a case where the thickness of the subject S is 100 mm, the distance between the X-ray irradiator 20 and each detector 32, 42 is 600 mm, the distance between the detector 32, 42 and the subject S (lower surface) is 10 mm, the distance between the X-ray irradiator 20 and the subject S (upper surface) is 490mm, the sensing width LW, HW of each detector 32, 42 is 0.8 mm, and the dead zone width NW of the dead zone region 82 is 0.4 mm. In addition, the X-ray irradiator 20 is arranged so as to be located above a middle portion of the dead zone region 82 between both detectors 32, 42. In this case, transmission X-rays to be irradiated to the sensing width of 0.8 mm have a width of approximately 0.787 mm at a position (lower irradiation plane R1*a*, R2*a*) 10 mm closer to the X-ray irradiator 20 from the detector 32, 42, and have a width of approximately 0.653 mm at a position (upper irradiation plane R1*b*, R2*b*) 110 mm closer to the X-ray irradiator 20 from the detector 32, 42. Then, as a result of making the lower irradiation planes R1*a* and R2*a* having the width of approximately 0.787 mm coincident, an overlap (shared region R3) in irradiation range between the low-energy side and the high-energy side results in approximately 70%. In addition, when, as shown in FIG. 11, the lower irradiation plane R1*a* of the region R1 and the lower irradiation plane R2*a* of the region R2 are not completely coincident (when, for example, there is 0.2 mm of mismatch in the above-described example), the shared part R3 therebetween is smaller than that shown in FIG. 10, and the overlap in irradiation range between the low-energy side and the high-energy side results in, for example, approximately 40%. in this case, mismatch between both energy images is increased, so that the detection accuracy of a foreign substance contained in the subject S may decline.

Figure 12:
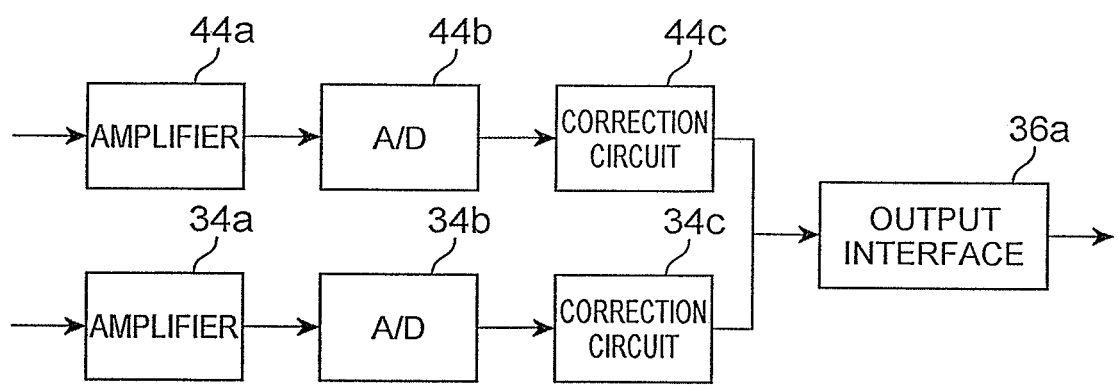
FIG. 12 is a diagram showing another embodiment of an energy image correcting section.

Moreover, in the above-mentioned embodiment, the low-energy image and the high-energy image are separately output, from the output interface 34*d* of the low-energy image correcting section 34 and the output interface 44*d* of the high-energy image correcting section 44, to the image processor 70, however, as shown in FIG. 12, both energy images may be output from a common output interface 36*a* to the image processor 70. Moreover, in the above-mentioned embodiment, there is provided a configuration including the low-energy detector 32 at an upstream side in the conveying direction A, and at a downstream side, a high-energy detector 42, however, the high-energy detector 42 may be provided at an upstream side in the conveying direction A, and the low-energy detector 32, at a downstream side. Further, in the above-mentioned embodiment, the detection, timing of the high-energy detector 42 is delayed by a predetermined time T, however, the detection timing of the low-energy detector 32 may be advanced by a predetermined time T conversely, or it may be possible to advance the detection timing of the low-energy detector 32 as well as delay the detection timing of the high-energy detector 42 so as to shift both detection timings by a predetermined time T. Moreover, in the above-mentioned embodiment, the detection timing in the two ranges of low energy and high energy is controlled, however, it may of course be possible to control the detection timing in three or more ranges.

Moreover, in the above-mentioned embodiment, a description has been given of the case where a low-energy wavelength range and a high-energy wavelength range have an overlap to some extent, however, a low-energy wavelength range and a high-energy wavelength range may not be partially overlapped. Moreover, in the above-mentioned embodiment, a description has been given in an example where two line sensors are provided on one chip, however, the two detectors 32, 42 do not need to he always provided on one chip, two independent detectors may be arranged in parallel to have a wider width of the dead zone region. Further, in the present embodiment, a spot source is used as the X-ray source, a line-shaped X-ray source may of course be used. Although, in the above-mentioned embodiment, the X-ray image acquiring system 1 is used for detection of the foreign substance O from the subject S, the X-ray image acquiring system 1 may be used for a baggage inspection etc.

What is claimed is:

1. A radiation detection device that detects radiation transmitted through a subject to which radiation is irradiated from a radiation source, comprising:
   a first detector that detects radiation that is transmitted through the subject to generate first radiation image data;
   a second detector that detects radiation that is transmitted through the subject to generate second radiation image data; and
   a timing control section that controls detection timing of at least one of the first detector and the second detector so that first radiation image data to be generated by the first detector and second radiation image data to be generated by the second detector mutually correspond,
   wherein the timing control section controls the detection timing of at least one of the first detector and the second detector, based on a magnification ratio being a ratio of a distance between the radiation source and the subject to a distance between the radiation source and the first detector or the second detector.

2. The radiation detection device according to claim 1, wherein the second detector is arranged in parallel to the first detector with a predetermined region sandwiched therebetween.

3. The radiation detection device according to claim 2, wherein the timing control section controls the detection timing of at least one of the first detector and the second detector, further based on a width of the predetermined region.

4. The radiation detection device according to claim 2, wherein the timing control section controls the detection timing of at least one of the first detector and the second detector, further based on a conveying speed at which the subject passes through the predetermined region.

5. The radiation detection device according to claim 2, wherein
   the first detector is a first line sensor that generates the first radiation image data in successive divided image data,
   the second detector is a second line sensor that generates the second radiation image data in successive divided image data, and
   the timing control section controls to delay the detection timing of at least one of the first line sensor and the second line sensor, based on a width of the predetermined region so that a detection range in the subject of divided image data by the first line sensor and a detection range in the subject of divided image data by the second line sensor are coincident.

6. The radiation detection device according to claim 2, wherein a width of the predetermined region is a width along a short-side direction of the first detector or the second detector and smaller than a sensing width to sense radiation in the first detector or the second detector.

7. The radiation detection device according to claim 2, wherein the timing control section controls the detection timing of at least one of the first detector and the second detector, further based on a delay time delaying the detection timing of the second detector relative to the detection timing of the first detector, the delay time being calculated based on a width of the predetermined region.

8. The radiation detection device according to claim 7, wherein the timing control section controls the detection timing of the second detector by outputting a control pulse signal to the second detector, the control pulse signal to the second detector being the same frequency as that of a control pulse signal to the first detector and being delayed in a rising spot of a pulse by the delay time.

9. A radiation image acquiring system comprising:
   the radiation detection device according to claim 2; and
   a timing calculating section that calculates the detection timing based on a width of the predetermined region.

10. The radiation image acquiring system according to claim 9, comprising a composite image generating section that generates a composite image by synthesizing radiation image data generated by the first detector and radiation image data generated by the second detector while being controlled by the timing control section so as to mutually correspond.

11. A radiation inspection system that irradiates radiation to a subject from a radiation irradiator and detects radiation transmitted through the subject to inspect the subject, comprising:
   a radiation irradiator that irradiates radiation to the subject;
   a first detector that detects radiation that is transmitted through the subject to generate first radiation image data;
   a second detector that detects radiation that is transmitted through the subject to generate second radiation image data;
   a conveying section that conveys the subject in a direction perpendicular to an irradiation direction of the radiation by the radiation irradiator;
   a timing control section that controls detection timing of at least one of the first detector and the second detector so that first radiation image data to be generated by the first detector and second radiation image data to be generated by the second detector mutually correspond when detecting radiation transmitted through the subject that is conveyed by the conveying section by the first detector and the second detector;
   a composite image generating section that generates a composite image by synthesizing first radiation image data generated by the first detector and second radiation image data generated by the second detector while being controlled by the timing control section so as to mutually correspond; and
   a composite image output section that outputs the composite image generated by the composite image generating section,
   wherein the timing control section controls the detection timing of at least one of the first detector and the second detector, based on a magnification ratio being a ratio of a distance between the radiation irradiator and the subject to a distance between the radiation irradiator and the first detector or the second detector.

12. The radiation inspection system according to claim 11, wherein the second detector is arranged in parallel to the first detector with a predetermined region sandwiched therebetween.

13. The radiation inspection system according to claim 12, wherein the timing control section controls the detection timing of at least one of the first detector and the second detector, further based on a width of the predetermined region.

14. The radiation inspection system according to claim 12, wherein the timing control section controls the detection timing of at least one of the first detector and the second detector, further based on a conveying speed of the subject by the conveying section.

15. The radiation inspection system according to claim 12, wherein a width of the predetermined region is a width along a short-side direction of the first detector or the second detector and smaller than a sensing width to sense radiation in the first detector or the second detector.

16. The radiation inspection system according to claim 12, wherein the timing control section controls the detection timing of at least one of the first detector and the second detector, further based on a delay time delaying the detection timing of the second detector relative to the detection timing of the first detector, the delay time being calculated based on a width of the predetermined region.

17. The radiation inspection system according to claim 16, wherein the timing control section controls the detection timing of the second detector by outputting a control pulse signal to the second detector, the control pulse signal to the second detector being the same frequency as that of a control pulse signal to the first detector and being delayed in a rising spot of a pulse by the delay time.

18. A radiation inspection method in a radiation detection device including a radiation source, a first detector, a second detector and a timing control section, the method comprising:
irradiating radiation to the subject from the radiation source;
detecting, by the first detector, radiation irradiated in the irradiating and transmitted through the subject to generate first radiation image data;
detecting, by the second detector, radiation irradiated in the irradiating and transmitted through the subject to generate second radiation image data; and
controlling, by the timing control section, detection timing in at least one of the detecting by the first detector and the detecting by the second detector so that first radiation image data to be generated in the detecting by the first detector and second radiation image data to be generated in the detecting by the second detector mutually correspond,
wherein, in the controlling, the timing control section controls the detection timing in at least one of the first detector and the second detector, based on magnification ratio being a ratio of a distance between the radiation source and the subject to a distance between the radiation source and the first detector or the second detector.

19. The radiation inspection method according to claim 18, wherein the second detector is arranged in parallel to the first detector with a predetermined region sandwiched therebetween and, in the controlling, the timing control section controls the detection timing of at least one of the first detector and the second detector, further based on a width of the predetermined region.

20. The radiation inspection method according to claim 18, wherein the second detector is arranged in parallel to the first detector with a predetermined region sandwiched therebetween and, in the controlling, the timing control section controls the detection timing of at least one of the first detector and the second detector, further based on a conveying speed at which the subject passes through the predetermined region.

* * * * *